(12) United States Patent
Germann et al.

(10) Patent No.: US 11,726,009 B2
(45) Date of Patent: Aug. 15, 2023

(54) METHOD AND DEVICE FOR MEASURING THE OXYGEN CONTENT OF THE HEADSPACE GAS IN A CONTAINER

(71) Applicant: ANTON PAAR GMBH, Graz-Strassgang (AT)

(72) Inventors: Klaus Germann, Graz-St. Peter (AT); Elisabeth Gangl, Graz (AT); Christof Umfer, Graz (AT)

(73) Assignee: Anton Paar GmbH, Graz-Strassgang (AT)

( * ) Notice: Subject to any disclaimer, the term of this patent is extended or adjusted under 35 U.S.C. 154(b) by 516 days.

(21) Appl. No.: 16/846,664

(22) Filed: Apr. 13, 2020

(65) Prior Publication Data

US 2020/0326264 A1    Oct. 15, 2020

(30) Foreign Application Priority Data

Apr. 12, 2019   (AT) .............................. A 50338/2019

(51) Int. Cl.
*G01N 1/22*       (2006.01)
*G01N 21/64*      (2006.01)
*G01N 27/416*     (2006.01)

(52) U.S. Cl.
CPC ....... *G01N 1/2226* (2013.01); *G01N 21/6428* (2013.01); *G01N 27/4162* (2013.01); *G01N 2001/2229* (2013.01); *G01N 2021/6432* (2013.01)

(58) Field of Classification Search
CPC combination set(s) only.
See application file for complete search history.

(56) References Cited

U.S. PATENT DOCUMENTS

| 4,926,681 | A  | * | 5/1990  | Fitzpatrick ........... G01N 1/2226 73/52 |
| 5,363,707 | A  |   | 11/1994 | Augenblick et al. |
| 7,100,460 | B2 |   | 9/2006  | Ozbal |
| 7,736,590 | B2 |   | 6/2010  | Matsuda et al. |
| 7,897,109 | B2 | * | 3/2011  | Labuda .............. G01N 21/6428 422/82.07 |
| 8,408,043 | B2 |   | 4/2013  | Stehle et al. |

(Continued)

FOREIGN PATENT DOCUMENTS

EP    0567782 A1    11/1993
EP    1887344 A1    2/2008

(Continued)

*Primary Examiner* — Peter J Macchiarolo
*Assistant Examiner* — Mohammed E Keramet-Amircolai
(74) *Attorney, Agent, or Firm* — Laurence A. Greenberg; Werner H. Stemer; Ralph E. Locher

(57) ABSTRACT

A device determines an oxygen content of a headspace gas in a liquid-filled container. The device contains a piercer, a sampling tube, a piercing head on which the piercer and the sampling tube are disposed, a pump, a ring line, and a sensor unit disposed within the ring line and used to determine the oxygen content and/or an oxygen partial pressure of the headspace gas of the liquid-filled container. The ring line is configured such that the headspace gas of the liquid-filled container can be sampled via the piercer or the piercing head by use of the pump and can be returned into the headspace of the liquid-filled container via the sampling tube.

20 Claims, 1 Drawing Sheet

(56) References Cited

U.S. PATENT DOCUMENTS

| | | | | |
|---|---|---|---|---|
| 2005/0223822 A1* | 10/2005 | Ozbal | ................ | G01N 35/1079 |
| | | | | 73/864.41 |
| 2009/0084156 A1* | 4/2009 | Matsuda | .............. | G01N 1/2226 |
| | | | | 73/19.1 |
| 2010/0236320 A1* | 9/2010 | Stehle | ................ | G01N 1/2226 |
| | | | | 73/19.1 |
| 2015/0247818 A1* | 9/2015 | Silvester | ................ | G01N 27/49 |
| | | | | 429/492 |
| 2016/0069919 A1* | 3/2016 | Holmes | ................ | G01N 21/51 |
| | | | | 435/14 |
| 2021/0208038 A1* | 7/2021 | Bellaton | ................ | G01N 3/04 |

FOREIGN PATENT DOCUMENTS

| | | |
|---|---|---|
| JP | H107115 A | 1/1998 |
| JP | H1010020 A | 1/1998 |
| WO | 2005100945 A1 | 10/2005 |
| WO | 2009050530 A1 | 4/2009 |

\* cited by examiner

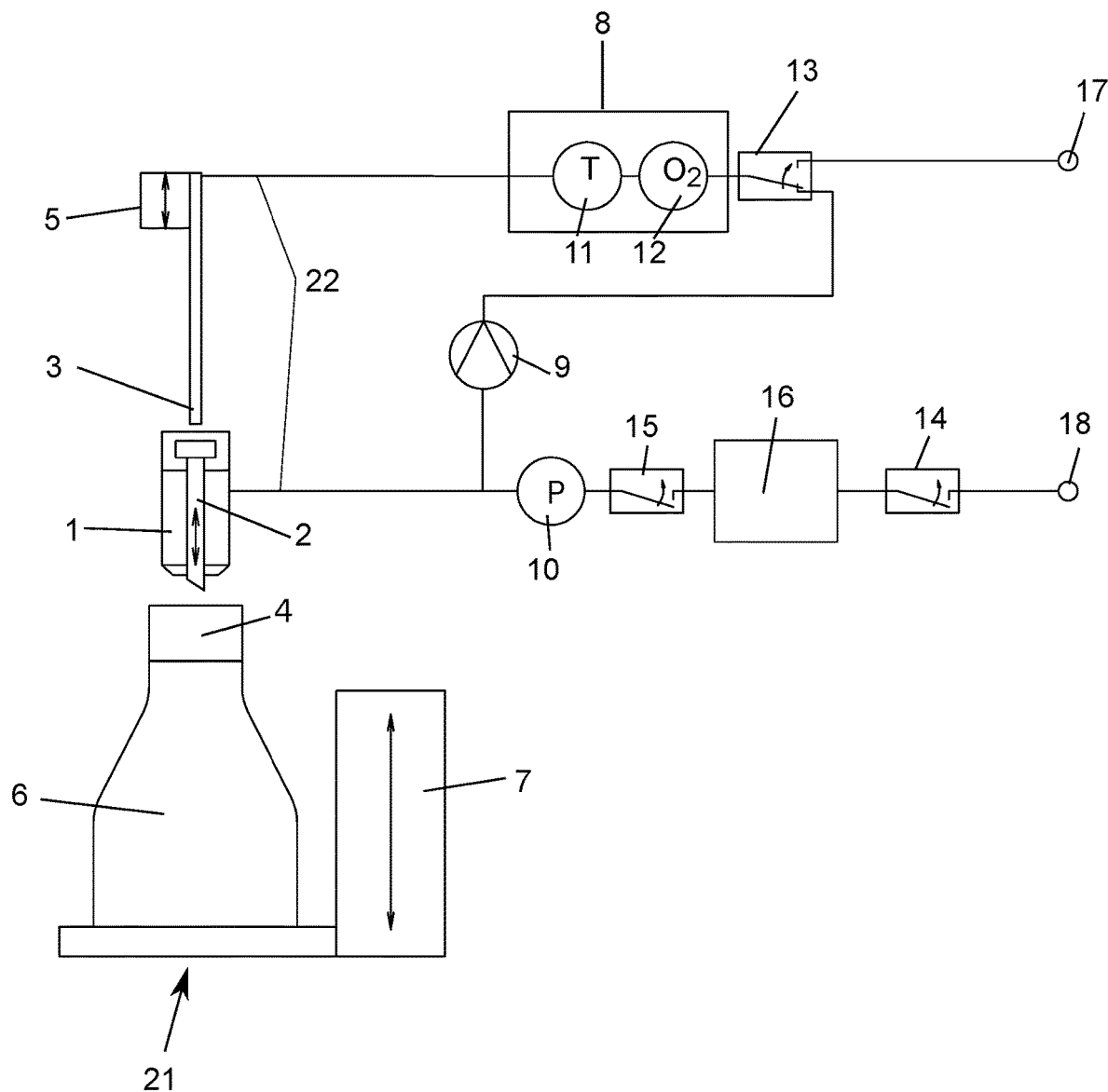

METHOD AND DEVICE FOR MEASURING THE OXYGEN CONTENT OF THE HEADSPACE GAS IN A CONTAINER

CROSS-REFERENCE TO RELATED APPLICATION

This application claims the priority, under 35 U.S.C. § 119, of Austrian application AT A50338/2019, filed Apr. 12, 2019; the prior application is herewith incorporated by reference in its entirety.

BACKGROUND OF THE INVENTION

Field of the Invention

The present invention relates to a method according to the preamble of the independent method claim and a device for carrying out the method according to the preamble of the independent device claim.

For beverage fillers, knowledge of the oxygen content in containers such as beverage cans, bottles and the like is of great interest, since the oxygen content influences the shelf life and taste of the beverage and, in the case of metal containers, their corrosion. In order to be able to draw conclusions about the cause of a possibly existing oxygen input, it is important to determine the oxygen content in the liquid and in the gas space above the liquid, the so-called headspace, separately.

In this way it can be determined whether the oxygen has got into the container together with the liquid or through a possibly poorly adjusted filling process. The measurement in the gas space is particularly important because, due to the low solubility of oxygen in aqueous liquids, there is a significant portion of the oxygen of the container in the headspace or the headspace gas. The measurement of the liquid sample is usually a trivial task, since the liquid sample can be drawn from the container via a hose line past an oxygen sensor. In general there is sufficient sample available to flush past the oxygen sensor until it shows a stable value after an adjustment time. The situation is more difficult when measuring headspace gas. There are usually only a few milliliters of headspace gas, which makes it difficult to flow the headspace gas past the oxygen sensor and discard it.

A number of measurement methods for measuring the oxygen concentration in the headspace are known from the prior art. Using a chemical method, the headspace gas, usually containing $CO_2$, $N_2$ and $O_2$, is passed through a soda solution that absorbs $CO_2$. The remaining volume then consists of $N_2$ and $O_2$, which is received with a composition of the ambient air and thus the oxygen content of the headspace gas is calculated. The disadvantage of the method is that an exact conclusion about the $O_2$ content is only possible if the headspace gas actually corresponds to the natural composition of air with approximate 20% oxygen. In general, however, this is not the case, since $N_2$ is used to flush the containers during filling and this changes the ratio of oxygen and nitrogen. Another disadvantage is that this method cannot be automated.

Furthermore, in the prior art, the oxygen content in the headspace gas is determined via the oxygen dissolved in the liquid. The prerequisite for this is that the container or the oxygen in the container has been brought into equilibrium in the liquid and the headspace gas by shaking and then the oxygen content of the liquid is determined. The disadvantage of the method is that it means that information is lost as to whether the oxygen has entered the container via the gas phase or the liquid phase. Another disadvantage is the complex shaking procedure, which takes at least 3 minutes.

Another known method for determining the headspace gas is to carry out the measurement directly in the headspace. With this method, the container is pierced and an oxygen sensor is introduced into the headspace. The disadvantage of the method is that in order to determine the oxygen content in this method, it is also necessary to know the temperature at the measurement location, since the sensor is highly temperature-dependent. Due to a lack of space, it is very difficult to place a temperature measurement at this point. Another disadvantage is that there is no flow in the headspace, which means that the adjustment of the sensor is very slow or does not take place completely. If there is foam in the headspace, e.g. in the case of beer, this measuring method no longer works reliably.

Another known method is to extract headspace gas. With this method, headspace gas is sampled flowing past an oxygen sensor. If equilibrium between liquid and headspace has previously been established using a suitable method, information about the total oxygen content can be obtained from this measurement. The disadvantage of the method is that the amount of gas is not sufficient to reliably achieve a stable adjustment of the oxygen sensor. Another disadvantage is that it is no longer possible to determine whether the oxygen was originally in the liquid or in the headspace.

BRIEF SUMMARY OF THE INVENTION

It is therefore an object of the present invention to provide a method of the type mentioned at the outset which overcomes the disadvantages of the prior art and thus enables a precise measurement of the oxygen content in the headspace gas separately from the oxygen content of the liquid and thereby reduces the duration of the measurement.

This object is achieved by the characterizing features of the independent method claim. It is provided that the headspace gas in the headspace of the container is pumped to a sensor unit containing a number of sensors, by means of a pump via the sampling tube and/or the hollow piercer and then back into the headspace of the container, and the oxygen content and/or the oxygen partial pressure and especially the headspace volume of the headspace gas is determined by the sensor unit.

It is achieved by the method according to the invention that, regardless of the headspace gas present, the oxygen content in it can be easily determined and a plurality of sensors can be used regardless of the free volume in the headspace. Furthermore, the sensors do not have to be introduced directly into the headspace, which simplifies the handling of the method. Sufficient headspace gas is also always available, since it is circulated or pumped back into the headspace, whereby a more precise determination of the oxygen content and/or the oxygen partial pressure and the headspace volume is achieved.

Particularly advantageous embodiments of the method according to the invention are defined in more detail by the features of the dependent claims.

It can advantageously be provided that, especially when measuring containers with foaming liquids, a foam is generated in the headspace of the container, in which the headspace gas or a portion of the headspace gas is bound, wherein the foam generated is led in the sensor unit and then again is returned into the headspace of the container. For example, even if only a small proportion of the headspace gas is present, the headspace gas bound in the foam or the oxygen contained therein can be easily determined, since due to the poor solubility of oxygen in aqueous substances, the oxygen content in the foam is a very good equivalent of the oxygen in the headspace.

For simple determination of the oxygen content and/or the oxygen partial pressure and/or the headspace volume, it can be provided that the sensor unit has an oxygen sensor for measuring the oxygen content and/or the oxygen partial pressure of the headspace gas. In particular, the oxygen content and/or the headspace volume are determined by additional measurement of the pressure by use of a pressure sensor and/or measurement of the temperature by use of a temperature sensor, preferably when a volume change of the headspace gas is brought about.

Since a plurality of sensors are temperature-sensitive or require a temperature adjustment to the medium to be measured in order to achieve maximum accuracy, it can be provided that the headspace gas is pumped from the headspace into the sensor unit, in particular passing the temperature sensor, and then pumped back into the headspace until the sensor unit, in particular the pressure sensor and the temperature sensor and the oxygen sensor, and/or the headspace gas reach a stable, preferably the same, temperature. By repeatedly pumping the headspace gas through the sensor unit, it is achieved that the individual sensors of the sensor unit can accept the temperature of the headspace gas or can be adjusted to this temperature and the measurements of the headspace gas can then be carried out in an adjusted temperature range. Furthermore, the temperature adjustment of the sensors or the sensor unit to the temperature of the headspace gas is accelerated in this way. In addition, other adjustment processes such as, for example, diffusion processes in the oxygen sensor have sufficient time for a complete adjustment.

In order to also be able to determine the oxygen content of the sample liquid, it can be provided that after the measurement of the oxygen content of the headspace gas, the sampling tube is lowered into the liquid in the container and then the liquid is sampled from the container and fed into the sensor unit, and so the oxygen content in the liquid is determined.

It can advantageously be provided that the sensor unit has a number of further sensors, in particular a $CO_2$ sensor, an alcohol sensor and/or a sugar sensor, wherein the $CO_2$ content and/or the alcohol content and/or the sugar content of the liquid in the container is determined by means of the further sensors. By arranging different sensors within the sensor unit or within the measuring arrangement, a wide variety of parameters of the sample liquid or the headspace gas can be determined, so that a complete analysis of the sample liquid and/or the headspace gas can be achieved. Alternatively, it can be provided that additional sensors are arranged outside the sensor unit in the line or the ring line.

The level of the sample liquid within the container can vary depending on the container and filling volume. Depending on the arrangement of the container, the headspace gas, which occurs again and again in beverage cans, for example, cannot be directly accessible and therefore cannot be pumped out directly via the removal opening. In order to make the availability of the headspace gas easier or to expand the headspace, it can be provided for the liquid level in the container to be lowered via the sampling tube before the measurement of the headspace gas in such a way that the headspace receives a direct connection to the sampling opening.

In order to be able to remove any existing oxygen or impurities from the sample arrangement or to better prevent falsification of the measurement results, before the measurement, it can be provided for the piercer, the piercing head, the sensor unit, the pump, the ring line and/or the sampling tube to be flushed with a flushing medium, in particular nitrogen, and thus are freed from oxygen and/or sample residues.

It can advantageously be provided that, prior to piercing the container, the pressure in the piercer and/or the piercing head and/or in the ring line, in particular by introduction of nitrogen gas, is adjusted to the internal pressure of the container so that foaming of the sample liquid is prevented. In this way, foam formation can be easily avoided and undesired leakage of the headspace gas can be prevented.

It can optionally be provided that after the container has been pierced, the oxygen sensor and/or temperature sensor, in particular via the sampling tube or the piercer, is introduced into the headspace of the container and the oxygen content and/or the temperature of the headspace gas is determined in the headspace. The pumping can thus quickly adjust the sensors and advantageously prevent the headspace gas from forming a layer.

It is a further object of the invention to create a device with which the oxygen content of the headspace gas can be easily determined.

This object is achieved by the features of the independent device claim. It is provided according to the invention that the device has a pump and a ring line, a sensor unit being arranged within the ring line with which the oxygen content and/or the oxygen partial pressure, and in particular also the headspace volume of the headspace gas of the container can be determined. The ring line is configured in such a way that the headspace gas of the container can be sampled by means of the pump via the hollow piercer or the piercing head and can be returned to the headspace of the container via the ring line, in particular via the sampling tube.

With the device according to the invention, the oxygen content or the oxygen partial pressure and/or the headspace volume can be determined easily and a high measuring accuracy is achieved.

It can advantageously be provided that the sensor unit has an oxygen sensor and/or a pressure sensor and/or a temperature sensor and/or a $CO_2$ sensor and/or an alcohol sensor and/or a sugar sensor, the oxygen sensor being configured in particular as an optochemical sensor based on the fluorescence quenching principle or as an electrochemical oxygen sensor.

An effective circulation of the headspace gas can easily be achieved by the pump being configured as a circulation pump, preferably as a diaphragm pump, peristaltic pump, piston pump, gear pump, worm pump, paddle wheel pump or syringe pump.

In order to be able to simply introduce a purge gas, such as, for example, nitrogen, into the device, it can be provided that the device has a number of valves integrated in the ring line, the valves being arranged in the ring line in such a way that the device, in particular the ring line, can be cleaned automatically via the valves.

Since the available piercing area is small, especially for containers with a narrow neck, a space-saving arrangement or design of the piercer and the sampling tube is advantageous. It can be provided according to the invention that the piercer is hollow, the sampling tube being introducible through the piercer into the sampling opening.

Further advantages and configurations of the invention result from the description and the accompanying drawings.

The invention is shown schematically below with reference to particularly advantageous, but not limiting, exemplary embodiments in the drawings and is described by way of example with reference to the drawings:

Other features which are considered as characteristic for the invention are set forth in the appended claims.

Although the invention is illustrated and described herein as embodied in a method for measuring the oxygen content of the headspace gas in a container, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

The single FIGURE of the drawing is a schematic representation of a device according to the invention.

DETAILED DESCRIPTION OF THE INVENTION

Referring now to the single FIGURES of the drawing in detail, there is shown a device according to the invention for determining the oxygen content of the headspace gas of a container is shown in a schematic view. The device contains a piercing head 1, on which a hollow piercer 2 is arranged. In this embodiment, the piercer 2 is configured like a needle and can be adjusted within piercing head 1 along the arrows shown. The device further has a sample holder 21, into which a container 6, in the embodiment of FIG. 1 a bottle, is inserted. The container 6 can be adjusted in the direction of the piercing head 1 by a drive 7, as a result of which piercing head 1 can be placed or attached to the sealed container 6. The device further has a sampling tube 3, which is arranged concentrically to piercer 2 in this embodiment. In this embodiment, the piercer 2 is hollow so that the sampling tube 3 penetrates the piercer 2 and can be brought through the piercer 2 into headspace 4. The sampling tube 3 is adjusted by means of a drive 5. Optionally, it can also be provided that the sample holder 21, the piercer 2, the piercing head 1 and/or the sampling tube 3 can be adjusted manually or in a controlled manner by a drive with a controller. At the end of the sampling tube 3 which is furthest away from the piercing head 1, a ring line 22 begins, which leads back into the piercing head 1 or opens into it again. A sensor unit 8 and a pump 9 are integrated in the ring line 22. By means of the pump 9, a sample liquid located in the container 6 or the headspace gas located in the headspace 4 of the container 6 can be sampled via the sampling tube 3 and thus supplied to the sensor unit 8. Via the sensor unit 8, the sample liquid or the headspace gas is returned through the pump 9 into the piercing head and thus back into the container 6 or into the headspace 4 of the container 6. Optionally, it can also be provided for the headspace gas and/or the sample liquid to be sampled via the piercing head and to be returned through the sampling tube 3 into the headspace 4 of the container 6.

In this embodiment, the sensor unit 8 contains a temperature sensor 11 and an oxygen sensor 12. The device further contains a pressure sensor 10 with which the pressure present in ring line 22 or the headspace 4 of the container 6 can be determined.

The method according to the invention is described below by way of example using the embodiment of FIG. 1.

In the method according to the invention, the container 6 or the piercing head 1 is adjusted so that the piercing head 1 is located on the container 6, for example at the lid of a bottle. Subsequently, the piercer 2 is adjusted in the direction of the container 6 and pierces for example the lid of the bottle and creates a sampling opening in the container 6. The sampling opening is covered in an airtight manner by sealing elements arranged on the piercer 2 and/or on the piercing head 1, so that no foreign gas can infiltrate the device or ring lines 22 or the headspace 4 of the container 6 and no gas can escape from the container 6. The sealing elements of the piercing head 1 or the piercer 2 thereby seal the container 6 and the ring lines in an airtight manner from the surroundings of the device. The sampling tube 3 is then lowered into the headspace 4 of the container 6 so that the sampling tube 3 penetrates into the headspace 4 without being immersed in the liquid or sample liquid of the container 6. The headspace gas is pumped out of the headspace 4 by means of the pump 9 via the sampling tube 3 and supplied to the sensor unit 8 via the ring line 22. In the sensor unit 8, the oxygen content and the temperature of the headspace gas are determined by means of the temperature sensor 11 and the oxygen sensor 12. The pressure in the headspace 4 is also determined by means of the pressure sensor 10 and the volume of the headspace gas is then determined, for example, using the gas equations. The headspace gas is then returned by the pump 9 via the ring line 22 from the sensor unit 8 via the piercing head 1 into the headspace 4 of the container 6. By circulating the headspace gas via ring lines, a circulation of the headspace gas within the device is brought about, so that the headspace gas can be pumped past the sensor unit 8 or the sensors of the device one or more times. By pumping the headspace gas past the sensor unit 8 or the sensors, the temperature adjustment of the sensors is improved, so that the determination of the oxygen content, the oxygen partial pressure and/or the headspace volume is accelerated and can be determined more precisely. Furthermore, the completion of sensor-specific adjustment processes, such as diffusion processes in the oxygen sensor, is completely awaited.

After determining the oxygen content of the headspace gas or the headspace volume or the oxygen partial pressure, the sampling tube 3 can be lowered further from the headspace 4 into the sample liquid of the container. The sample liquid is then pumped to the sensor unit 8 and the oxygen content, the temperature and the pressure of the sample liquid are also determined.

Since the containers 6 with foaming liquids tend to foam after being pierced by means of the piercer 2, in particular when inserted quickly into the sample holder 21, for example, the foam formation in the headspace 4 of the container 6 can be intentionally increased or a foam can only be generated in that the headspace gas or a portion of the headspace gas is bound. The foam generated can then be supplied to the sensor unit 8 by means of the pump 9 via the ring lines 22 and the oxygen content of the foam can thus be determined. Since the oxygen content of the foam corresponds to that of the headspace 4 or the headspace gas, the oxygen content of the headspace gas can thus be determined.

Since the sensors usually have a temperature-dependent measurement behavior, and an adjustment behavior caused by various physical effects, it is advantageous that the sensors, in particular oxygen sensor 12 and temperature sensor 11, are adjusted to the temperature of the headspace gas or the sample liquid, or to wait for other adjustment processes to take place. In order to be able to carry out this adjustment quickly, the headspace gas 4 is optionally pumped past the sensor unit 8 or the sensors several times, thus accelerating the adjustment. By circulating the headspace gas or by repeatedly pumping the headspace gas, even small amounts of the headspace gas can be measured by means of the sensor unit 8, or a rapid adjustment of the sensors to the headspace gas and the sample liquid can be achieved even with small amounts of the headspace gas.

The device further contains a valve 13 arranged in the ring line 22, which is connected to a line leading into the surroundings at a flushing opening 17. Via the flushing opening 17, for example, a flushing gas such as nitrogen or a cleaning solution can get into the ring line or to the sensor unit 8 or the pump 9 and the sensors and thus sample residues or residual oxygen can be flushed out of the device.

Optionally, it can be provided that, as shown in FIG. 1, the device contains a number of further valves 14, 15 and a storage volume 16. Storage volume 16 is connected to pressure sensor 10 via valve 15 and connected to the surroundings of the device via a further valve 14.

Since the headspace gas originally located only in the headspace 4 can be distributed in the ring line 22 when the container 6 is opened by the piercer 2, lower $O_2$ concentrations are measured than were present in the headspace 4 of originally closed the container 6. This systematic error is corrected by calculation. To this end, the pump circuit volume or the volume of the ring lines 22 and the components connected thereto must be known and of the headspace volume must be known. The headspace volume is determined in the course of the measurement process by the sensor unit 8 or the pressure sensor 10 and the temperature sensor 11 and/or determined by using the gas laws.

For this purpose, an empty storage volume 16 is integrated in the device of the embodiment of FIG. 1. In a first step before the container 6 is pierced, the valve 14, which is connected to the surroundings of the device via an air inlet 18, is opened and the storage volume 16 is brought to ambient air pressure. If the valve 15, which connects the storage volume to the ring line 22, is open, a first air pressure p1 can be measured. Now the valves 14 and 15 are closed. After piercing the container 6 by the piercer 2, the pressure p2 is measured, which results from the combination of the pressure of pierced the container 6 and the pressure applied in the piercing head 1 and the ring lines 22. Then, the valve 15 is opened and the resulting mixing pressure p3 is measured. If the storage volume 16 is known, the headspace volume $V_{Headspace}$ can now be calculated using Boyle Mariotte's law (equation 1):

$$V_{Headspace} = V_{Expansion} \times \frac{p_3 - p_2}{p_1 - p_3} - V_{Apparatus}. \qquad \text{Equation 1}$$

Since the expansion is neither purely isothermal nor purely adiabatic, the result is only a good approximation.

The expansion volume $V_{Expansion}$ and the apparatus volume $V_{Apparatus}$, i.e., the volume in the device or in the ring line 22, the sampling tube 3, the piercer 2 and the piercing head 1, can be determined from the design, however, it is better if various known headspace volumes $V_{Headspace}$ are used to carry out a series of measurements and, based on those measurements the $V_{Expansion}$ and $V_{Apparatus}$ are calculated. In addition to the geometry information, the two values then contain corrections for deviations from the isothermal behavior and can thus enable an even more precise result of the measurement.

The measured oxygen concentration can then be corrected using the known volumes using equation 2:

$$O_{2,corr} = O_{2,measured} \frac{V_{Apparatus} + V_{Headspace}}{V_{Headspace}}. \qquad \text{Equation 2}$$

Alternatively, at the start of the measurement, the storage volume 16 can also be brought to a higher pressure than that prevailing in the container 6. For this purpose, the piercing head 1 is sealed with the piercer 2 to the container 6 before piercing. Then, the valves 14 and 15 are opened so that the same pressure prevails in the entire area between the air inlet 18 and the piercing head 1. This pressure is measured with the pressure sensor 10. The valves 14 and 15 are then closed and the pressure is thus "locked in" in the storage volume 16. The remaining method for measuring the oxygen concentration is then carried out analogously to the method described above.

Alternatively, it can be provided that the headspace gas or the sample liquid is pumped into the ring line 22 out via the piercer 2 or the sampling tube 3 connects directly to the piercer 2. Alternatively, after opening or piercing the bottom 20 of the container 6, the piercer 2 can remain in the headspace 4 and the headspace gas or the sample liquid can be pumped into the ring line 22.

Optionally, the sensor unit 8 or the device can also have a number of further sensors, for example a $CO_2$ sensor, an alcohol sensor, a sugar sensor and/or further sensors, which are integrated in the ring line 22 or the sensor unit 8. The further sensors can be used, for example, to determine the $CO_2$ content or the alcohol content or the sugar content of the sample liquid and thus determine further parameters of the sample liquid. The further sensors can optionally also be filled with the sample liquid via the opening 17. The further sensors can, for example, provide further information during the production of beverages such as beer or lemonades, so that the quality control of the filling process or of the production process can be easily monitored by means of the device according to the invention.

The oxygen sensor 12 can in particular be configured as an optochemical sensor based on the fluorescence quenching principle or, for example, as an electrochemical oxygen sensor. Optionally to the embodiment shown in FIG. 1, the sensor unit can also contains only one oxygen sensor 12, with which the oxygen content of the headspace gas and/or the sample liquid is determined.

The pump 9 of the embodiment shown in FIG. 1 can be configured, for example, as a circulation pump, in particular as a diaphragm pump, peristaltic pump, piston pump, gear pump, worm pump, paddle wheel pump or syringe pump.

Optionally, the drive 7 or the adjustment mechanisms of the piercer 2 and the sampling tube 3 can be driven manually or in a different manner, thus causing the individual parts to be displaced relative to one another.

Alternatively, it can be provided that instead of arranging the oxygen sensor 12 within the ring line 22 or the sensor arrangement 8, the oxygen sensor 12 is introduced into the headspace 4 of the container 6 via the sampling tube 3 or the piercer 2. The headspace gas can then be circulated via the ring line 22 and thus the adjustment of the sensors can be improved or accelerated by the circulation of the headspace gas. Optionally, the temperature sensor 11 can also be introduced into the headspace 4.

The invention claimed is:

1. A method for measuring an oxygen content and/or an oxygen partial pressure of a headspace gas in a liquid-filled container, which comprises the steps of:
   using a hollow piercer disposed on a piercing head for introducing a sampling opening in the liquid-filled container and into the sampling opening a sampling tube penetrates, and the sampling opening being covered in an airtight manner by means of sealing elements disposed on the hollow piercer or the piercing head; and
   pumping a headspace gas in a headspace of the liquid-filled container into a sensor unit having a plurality of sensors, by means of a pump via the sampling tube and/or the hollow piercer and or the piercing head and then back into the headspace of the liquid-filled container and thus the oxygen content and/or the oxygen partial pressure and/or a headspace volume of the headspace gas is determined by the sensor unit.

2. The method according to claim 1, wherein when measuring the liquid-filled container filled with a foaming liquid, generating a foam in the headspace of the liquid-filled container in which the headspace gas or a portion of the headspace gas is bound, wherein the foam generated is led into the sensor unit, and subsequently returned to the headspace of the liquid-filled container.

3. The method according to claim 1, wherein the sensor unit has an oxygen sensor for measuring the oxygen content and/or the oxygen partial pressure of the headspace gas.

4. The method according to claim 3, wherein the oxygen content and/or the headspace volume are determined by an additional measurement of a pressure by means of a pressure sensor and/or a measurement of a temperature by means of a temperature sensor, when a volume change of the headspace gas is brought about.

5. The method according to claim 3, which further comprises:
   pumping the headspace gas from the headspace into the sensor unit and passing the temperature sensor and/or the oxygen sensor; and
   pumping back the headspace gas into the headspace until the sensor unit, namely the pressure sensor and/or the temperature sensor and/or the oxygen sensor, and/or the headspace gas reach a stable, same temperature.

6. The method according to claim 1, which further comprises:
   pumping the headspace gas from the headspace into the sensor unit; and
   pumping back the headspace gas into the headspace until the sensor unit and/or the headspace gas reach a stable temperature.

7. The method according to claim 1, wherein after a measurement of the oxygen content of the headspace gas, lowering the sampling tube into a liquid in the liquid-filled container and then the liquid is sampled from the liquid-filled container and passed into the sensor unit, and the oxygen content in the liquid is determined in this way.

8. The method according to claim 1, wherein the sensor unit has a plurality of further sensors, and a $CO_2$ content and/or an alcohol content and/or a sugar content of a liquid in the liquid-filled container is determined by means of the further sensors.

9. The method according to claim 1, wherein before a measurement of the headspace gas, lowering a liquid level in the liquid-filled container via the sampling tube such that the headspace receives a direct connection to the sampling opening.

10. The method according to claim 1, wherein before performing a measurement, flushing the piercer, the piercing head, the sensor unit, the pump, a ring line and/or the sampling tube with a flushing medium, and thus are freed from oxygen and/or sample residues.

11. The method according to claim 1, wherein prior to piercing the liquid-filled container, adjusting a pressure in the piercer and/or the piercing head and/or in a ring line, to an internal pressure of the liquid-filled container so that foaming of a sample liquid is prevented.

12. The method according to claim 1, wherein after piercing of the liquid-filled container, introducing an oxygen sensor and/or a temperature sensor in the headspace of the liquid-filled container and the oxygen content and/or a temperature of the headspace gas in the headspace are determined.

13. The method according to claim 1, wherein the sensor unit has a $CO_2$ sensor, an alcohol sensor and/or a sugar sensor.

14. A device for determining an oxygen content of a headspace gas in a liquid-filled container, the device comprising:
   a piercer;
   a sampling tube;
   a piercing head on which said piercer and said sampling tube are disposed;
   a pump;
   a ring line; and
   a sensor unit disposed within said ring line and used to determine the oxygen content and/or an oxygen partial pressure of the headspace gas of the liquid-filled container, said ring line being configured such that the headspace gas of the liquid-filled container can be sampled via said piercer or said piercing head by means of said pump and can be returned into the headspace of the liquid-filled container via said sampling tube.

15. The device according to claim 14, wherein said sensor unit has an oxygen sensor and/or a pressure sensor and/or a temperature sensor and/or a $CO_2$ sensor and/or an alcohol sensor and/or a sugar sensor.

16. The device according to claim 15, wherein said oxygen sensor is configured as an optochemical sensor based on a fluorescence quenching principle or as an electrochemical oxygen sensor.

17. The device according to claim 14, wherein said pump is a circulation pump.

18. The device according to claim 17, wherein said circulation pump is selected from the group consisting of a diaphragm pump, a peristaltic pump, a piston pump, a gear pump, a worm pump, a paddle wheel pump or a syringe pump.

19. The device according to claim 14, further comprising a plurality of valves integrated in said ring line, said valves being disposed and formed in said ring line such that an automatic cleaning of the device and/or a flushing with a flushing gas and/or a filling of said ring line and/or a sampling of liquids can take place via said valves.

20. The device according to claim 14, wherein:
   said piercer is hollow; and
   said sampling tube can be introduced through said piercer into a sampling opening in the liquid-filled container.

* * * * *